(12) United States Patent
Ward et al.

(10) Patent No.: US 7,919,589 B2
(45) Date of Patent: Apr. 5, 2011

(54) METHOD FOR REMOVING ENDOTOXIN FROM PROTEINS

(75) Inventors: Loren S. Ward, Twin Falls, ID (US);
Kevin Thomson, Fitchburg, WI (US);
Stanley Wrobel, Twin Falls, ID (US)

(73) Assignee: Glanbia Nutritionals (Ireland), Ltd., Kilkenny (IE)

( * ) Notice: Subject to any disclaimer, the term of this patent is extended or adjusted under 35 U.S.C. 154(b) by 14 days.

(21) Appl. No.: 12/171,264

(22) Filed: Jul. 10, 2008

(65) Prior Publication Data

US 2009/0029921 A1    Jan. 29, 2009

Related U.S. Application Data

(60) Provisional application No. 60/948,839, filed on Jul. 10, 2007.

(51) Int. Cl.
*C07K 1/00* (2006.01)
(52) U.S. Cl. ...................................................... 530/350
(58) Field of Classification Search ................... 530/350
See application file for complete search history.

(56) References Cited

FOREIGN PATENT DOCUMENTS

WO       2005/003152    *   1/2005

* cited by examiner

*Primary Examiner* — Maryam Monshipouri
(74) *Attorney, Agent, or Firm* — Donna Russell (57) ABSTRACT

Disclosed is a method for removing endotoxin from proteins. Also disclosed are products made by using the method. The method may be used, for example, to produce endotoxin-free lactoferrin. Bovine milk-derived lactoferrin may be produced in commercial quantities by the method, and endotoxin-free bovine lactoferrin may be used for a variety of therapeutic uses, including improving wound healing.

5 Claims, 6 Drawing Sheets

METHOD FOR REMOVING ENDOTOXIN FROM PROTEINS

This application claims the benefit of priority of earlier-filed U.S. provisional application No. 60/948,839, filed Jul. 10, 2007.

FIELD OF THE INVENTION

The invention relates to methods for removing endotoxin from proteins. More specifically, the invention relates to methods for removing endotoxin from proteins which bind endotoxin and to products produced by that process.

BACKGROUND OF THE INVENTION

The term "endotoxin" is most commonly used to refer to a lipopolysaccharide complex associated with the outer membrane of Gram-negative bacteria, although a variety of microorganisms have "endotoxin-like" components. Endotoxin is associated with a variety of negative effects on cells and tissues, including promoting cell death and triggering proinflammatory cytokines and nitric oxide. At sufficient levels in the body, endotoxin can produce "toxic shock," a life-threatening condition. Nakagawa et al. (Nakagawa, Y. et al. "Endotoxin Contamination in Wound Dressings Made of Natural Biomaterials, *J. Biomed. Mater. Res. Part B: Appl. Biomater.* 66B: 347-355, 2003) demonstrated that endotoxin contamination in nine different natural wound dressings could produce fever in rabbits.

A variety of methods have been developed for removing endotoxin from proteins. These methods, however, do not lend themselves to the production of large quantities of endotoxin-free compositions. For years, complete endotoxin removal was usually achieved only with massive loss of substrate protein during the process. More recently, products have been developed for increased endotoxin removal with significant recovery of the substrate protein, but to date these products and the methods upon which they are based have not been suitable for the production of large quantities of endotoxin-free protein in a cost-effective manner. Some methods, such as that described by Naidu (U.S. Pat. No. 7,125,963) utilize a multi-step, multi-reagent approach to endotoxin removal. For some products, it is desirable to limit the use of some of these reagents, such as detergents/surfactants, which can be costly when used in large quantities. Thus such a method may be cost-prohibitive for preparation of some products.

Lactoferrin is a multi-functional protein belonging to the transferrin family of proteins. It is an 80 kDa protein, found primarily in milk and mucosal secretions. Lactoferrin binds iron, heparin, proteoglycan, DNA, oligodeoxynucleotides, and LPS (endotoxin). Two LPS binding sites have been identified in lactoferrin, the 28-34 loop region and an N-terminal four arginines (residues 2-5). The effectiveness of lactoferrin against the biological effects of endotoxins has been demonstrated. However, lactoferrin readily binds endotoxin—and it would be desirable to remove the bound endotoxin and improve the overall benefit that lactoferrin can provide. Furthermore, it would be beneficial to develop methods for removing endotoxin from large quantities of a variety of different proteins, and especially from those proteins that bind endotoxin.

SUMMARY OF THE INVENTION

The invention relates to a method for removing endotoxin from a protein composition and to products made (purified) by the method. In certain aspects, the invention relates to a method for removing endotoxin from protein, the method comprising binding the protein to a cationic exchange resin, eluting the endotoxin from the bound protein using a low ionic strength (i.e., low salt) solution without added surfactant, and eluting the protein from the resin using a high ionic strength solution such as high salt, acid, or other suitable compositions. In certain aspects, the method may further comprise the steps of filtering the eluted protein and drying the product of the ultrafiltration step. The method may also comprise using fractal distribution to apply the protein with bound endotoxin, the low ionic strength solution, and the high ionic strength solution to a cation exchange column.

In one aspect, the invention relates to a method for removing endotoxin from lactoferrin, lactoferricin, lactoperoxidase, and/or other endotoxin-binding proteins, as well as to endotoxin-free products, such as endotoxin-free lactoferrin (EFL), produced by the method. When isolated from milk or a milk fraction, such a product may also comprise additional milk-derived factors having desirable properties, such as, for example, glycomacropeptide, growth factors, or other proteins, lipids, etc., and particularly those bovine milk-derived agents having endotoxin-binding or endotoxin-neutralizing activity. Compositions of the invention may also comprise EFL and xylitol, optionally supplemented with an antimicrobial composition comprising silver.

The invention also relates to methods for treating an acute wound and for treating biofilm-associated disease conditions, including chronic wounds, comprising administering a composition comprising a therapeutically-effective amount of an endotoxin-free bovine milk-derived lactoferrin.

Methods may also comprise administering additional active agents such as, for example, activated lactoferrin, xylitol, an antimicrobial silver composition, or a combination thereof.

DETAILED DESCRIPTION

The inventors have developed a novel method for removing endotoxin from a protein. The method does not require the use of detergents/surfactants and, unlike currently available methods, is suited for producing kilogram quantities of endotoxin-free protein in a cost-effective manner. The method of the invention may be readily used to produce large (e.g., kilogram) quantities of bovine lactoferrin from milk or milk fractions, for example. The inventors have used the method to remove endotoxin from lactoferrin, and thereby produced an endotoxin-free lactoferrin (EFL) product. As used herein, the term "endotoxin-free" is intended to describe lactoferrin compositions comprising less than about 20 endotoxin units per milligram of protein (EU/mg), more preferably less than about 10 EU/mg, and even more preferably less than about 1 EU/mg, so the composition, as compared to lactoferrin isolates in the current commercial market, is substantially endotoxin-free. Included in the products made by the process of the invention are products made from sweet whey having from about 0 to about 20 EU/mg, products having from about 0 to about 15 EU/mg, products having from about 0 to about 10 EU/mg, products having from about 0 to about 5 EU/mg, and products having less than 1 EU/mg, for example. Currently available commercial products, for example, may have at least about 20 EU/mg lactoferrin if derived from milk and at least about 250 EU/mg lactoferrin if derived from sweet whey. For EFL products derived from milk, "endotoxin-free" is intended to comprise EFL products having less than or equal to 1 EU/mg.

Commercial products comprising lactoferrin isolated from milk and milk fractions are produced by a number of companies. Tests of those products, however, demonstrate that such lactoferrin products contain amounts of endotoxin associated with the lactoferrin that are significant when viewed in the context of treatment of wounds, particularly (see Table 1). The method of the present invention provides a means by which large quantities of EFL may be produced from bovine milk and/or one or more milk fractions, for example, yielding a product that has significantly lower endotoxin levels and has been demonstrated to provide a more beneficial effect to cells that inhabit the wound environment than do bovine milk-derived lactoferrin products presently available in the market.

TABLE 1

Levels of Lactoferrin-Associated Endotoxin in Commercial Milk-Derived Lactoferrin Isolates

| Product Number | Lactoferrin Source | Endotoxin Level (expressed as endotoxin units per milligram) |
|---|---|---|
| 1 | Sweet whey | 1000-1250 EU/mg |
| 2 | Sweet whey | 250-300 |
| 3 | Sweey whey | 250-300 |
| 4 | Milk | 20 |

Previously described methods for removing endotoxin from proteins such as lactoferrin, for example, relied on the use of surfactants to aid in separation of the bound endotoxin from the lactoferrin. Surfactants, however, are expensive and the use of surfactants to remove endotoxin from protein is cost-prohibitive when larger-scale processes are required in order to make commercial quantities of endotoxin-free protein. The inventors have discovered that the use of a combination of low-ionic strength (e.g, low salt) solution used to elute endotoxin from a protein that is tightly bound to a cation exchange column, followed by elution of the protein with a high ionic strength (e.g., high salt, acid, etc.) solution, eliminates the need for the surfactant. Low salt solutions may comprise, for example, 0.01 to 0.5 molar salt solutions and in some embodiments may comprise, for example, 0.25 to 0.35 molar salt solutions. Methods for making such solutions and for selecting the appropriate ionic strength, molarity, etc. for ion exchange methods, are known to those of skill in the art.

Lactoferrin binds a number of compounds, including iron, heparin, proteoglycan, DNA, oligodeoxynucleotides, and LPS (endotoxin). Two LPS binding sites have been identified in lactoferrin, the 28-34 loop region and an N-terminal four arginines (residues 2-5). The effectiveness of lactoferrin against the biological effects of endotoxins has been demonstrated. Lactoferrin is especially effective for the inhibition of biofilm reconstitution in a chronic wound, and compositions of the present invention may be used in methods for inhibiting both biofilm formation and reconstitution. Such compositions may also provide effective treatment for acute wounds in which biofilm has not yet developed, since the endotoxin provided by a lactoferrin composition other than an EFL is detrimental to primary human keratinocytes and is known to produce a triggering effect on the inflammatory response, which may actually delay wound healing. Non-EFL compositions may therefore not provide as rapid a wound-healing response as do EFL compositions.

The method for removing endotoxin from a protein comprises the steps of passing a liquid composition comprising the protein with bound endotoxin through a cation exchange system to bind a protein to the cation exchange resin, eluting the endotoxin from the protein using a low-ionic strength solution such as, for example, a low salt solution, eluting the protein from the cationic exchange resin using a high-ionic strength solution such as, for example, a high salt solution, one or more acids, etc., optionally followed by the steps of filtering the eluted protein and drying the protein. Drying the protein may be accomplished using methods know to those of skill in the art, such as freeze-drying, spray-drying, etc. Filtration may be performed, for example, using ultrafiltration methods known to those of skill in the art. In some embodiments, the step of binding the protein to the cation exchange resin may be performed using a cation exchange column such as those manufactured and/or made commercially available by BioRad, Amalgamated Research, Inc., and others. The inventors recommend that the cation exchange resin be selected to tightly bind the protein to be purified in order to maximize the efficiency of the process.

Figure 1:
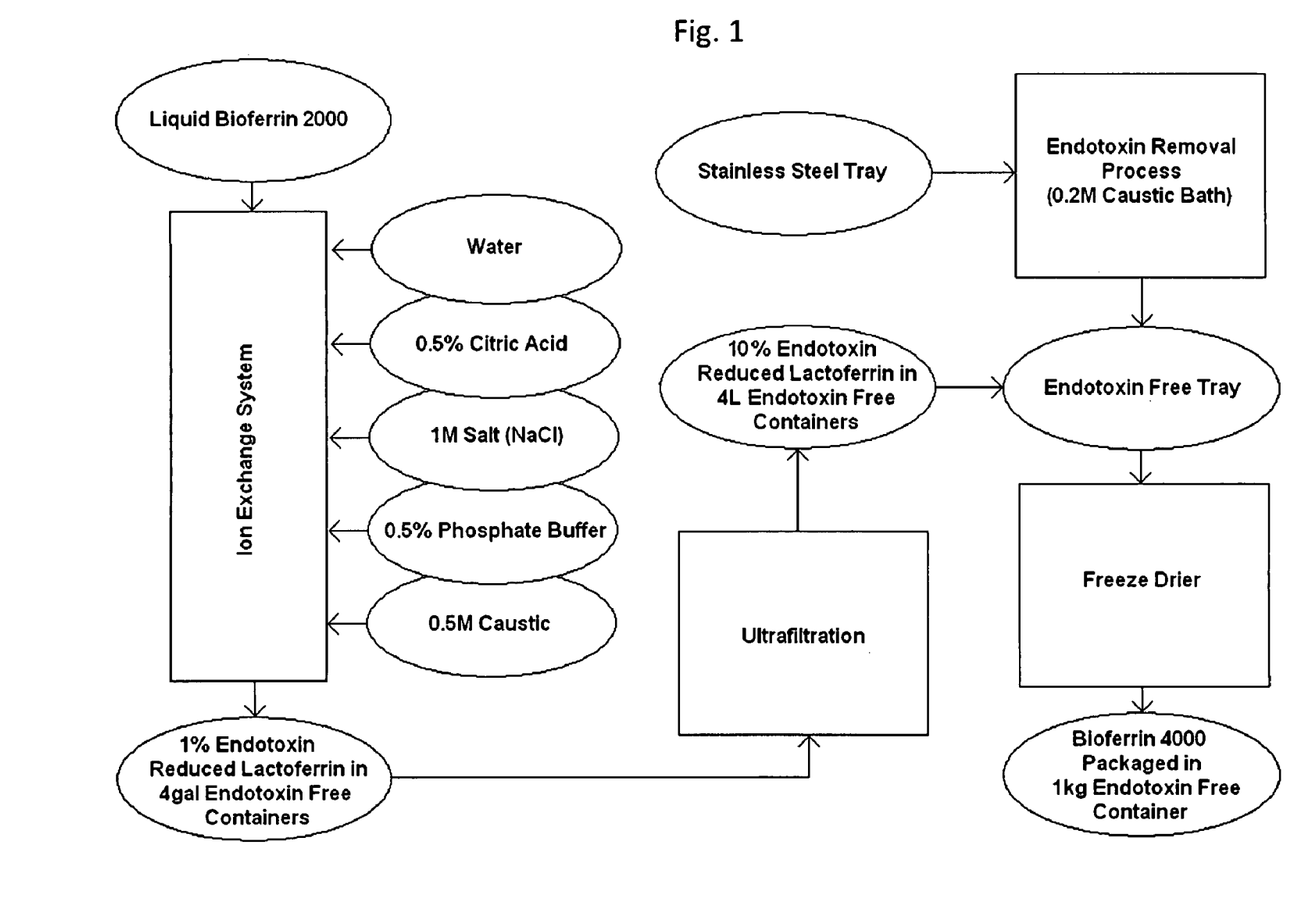
FIG. 1 is a flow chart describing one embodiment of the present method for removing endotoxin from a protein composition.

The method may be performed according to the following example. Process conditions are suggested, but are not intended to be limiting, as it is well within the skill of those in the art to modify these process conditions, depending upon the cation exchange system used, the ultra-filtration system/method used, etc. The inventors suggest that all processes be performed at or below 40 degrees Fahrenheit in order to limit potential microbial contaminant growth. This process may also be illustrated by the flow chart in FIG. 1. Briefly, an ion exchange column, such as a 300 mm×200 mm ARi custom ion exchange column (Amalgamated Research, Inc.) with fractal distribution heads and having a column volume of approximately 9.5 L, is prepared for loading by the addition of at least 3 or more column volumes of caustic agent (0.2N) at a flow rate of 400-500 liters per hour, followed by down flow or no flow prior to the addition of buffer (e.g., phosphate buffer, 1% at pH 6-7.5) with a flow rate of 50-400 liters per hour to flush until the pH reaches less than about 8. Salt is then added as a 1 molar 80-100 mS/cm solution and the flow rate is adjusted to about 50-400 liters per hour for one or more column volumes (preferably 2) and the column is flushed with water at a flow rate of 50-500 liters per hour. For all the above steps, a flow rate of 300 liters per hour for a column such as the ARi 300 mm×200 mm is recommended. As is known to those of skill in the art, various column sizes may be used and volumes adjusted accordingly.

The column is then loaded with a liquid lactoferrin composition (5-10%), one example of such a composition being commercially available and sold as Bioferrin 2000 (Glanbia Nutritionals, Inc., Monroe, Wis.). The liquid lactoferrin composition may be derived or obtained from a variety of sources, including sweet whey, milk, and/or milk fractions, for example, and may include various forms of lactoferrin such as metal-saturated (holo) lactoferrin and metal-free (apo) lactoferrin. Other proteins and milk-derived substances may also be included in a liquid lactoferrin composition, but such a composition will preferably be an enriched lactoferrin composition or a purified lactoferrin composition. For the column described above, 1.5 to 20 liters of liquid lactoferrin composition is loaded onto the column, with 10 liters being recommended. Flow rate is adjusted to 50 to 400 liters per hour (100 liters per hour recommended), down flow. The column is then flushed with one or more column volumes of water at a flow rate of 50-400 liters per hour. Without being bound by theory, the inventors believe that fractal distribution provides an added benefit for the removal of endotoxin via ion exchange, such as in the cation exchange method described herein.

Next, a low salt solution (28-37 mS/cm) is added to the column and flow is adjusted to 50-400 liters per hour (150 liters per hour recommended) so that the low salt solution is run through the column at 2 or more column volumes. A high salt solution (80-100 mS/cm) is then added at one or more column volumes (1.4 recommended), and flow is adjusted to 50-400 liters per hour (200 liters per hour recommended). The column is then flushed with water at one or more column volumes and a flow rate of 50-400 liters per hour (360 liters/hour recommended), followed by a citric (0.5% citrate) flush upflow for 1 or more column volumes at a flow rate of 50 to 400 liters/hour (300 L/hr preferred). The citrate flush upflow is followed by a citrate flush downflow of 3 or more column volumes at a flow rate of 50-400 liters/hour (preferably 300 liters/hour).

A water flush is then performed using at least two column volumes of water at a flow rate of 50-400 liters/hour (400 L/hr), followed by the addition of a high salt solution (80-100 mS/cm) for 1 or more column volumes at a volume of 50-400 liters/hour (300 L/hr). At least two column volumes of water is then run through the column. Endotoxin-free protein (lactoferrin) is collected in suitable containers such as sterilized buckets, stainless steel tanks, etc.

Product from the ion exchange system is then subjected to ultra-filtration. Briefly, the endotoxin-reduced product from the ion exchange system is transferred into a refrigerated balance tank until full, or until the desired batch quantity is achieved. The ultra-filtration system (10 kDa membrane) is operated at 40° F. or less. Product is concentrated to about 4% solids and diafiltration water is then added until the conductivity of the retentate is less than 8.0 mS/cm. Liquid is drained into an endotoxin-free container and kept at a temperature of less than about 40° F. The ultrafiltration device is cleaned using Ecolab AC-55-5 acid cleaner (500 ml/25 gal), which is circulated for at least 30 minutes to 1 hour. Caustic is used to clean by circulating 0.2M for at least 6 hours, and preferably for 12 hours. Next, the system is rinsed with endotoxin-free water (0.2 EU/ml) until the pH is less than 8.0. (Water filtration is performed using a Flow Solutions AB3NFZ7PH4 system.)

For freeze-dried product, all product contact surfaces should be soaked with 0.2M caustic for at least 6 hours, and preferably 12 hours or more, followed by thorough rinsing with endotoxin-free water prior to making contact with the product. A suitable method for drying the product may be chosen from among methods known to those of skill in the art, including, for example, freeze-drying, spray-drying, and other methods. The resulting powder may be packaged into one or more suitable endotoxin-free containers.

Methods for purification and isolation of LF from a variety of sources have been described, for example, in U.S. Pat. Nos. 4,190,576; 4,436,658; 4,667,018; 4,668,771; 4,791,193; 4,997,914; 5,087,369; 5,149,647; 5,169,936; 5,179,197; 5,516,675; 5,571,896; 5,596,082; 5,756,680; 5,849,885; 5,861,491; 5,919,913; 6,010,698; 6,096,870 and 6,268,487. Liquid lactoferrin compositions for use in the method may comprise any lactoferrin-containing composition, but preferably comprise an enriched concentration (i.e., greater than 2%) of lactoferrin. Lactoferrin may be isolated directly from milk, or may be isolated from milk fractions such as whey and/or whey protein isolate, for example. In industry terms, such a lactoferrin product would be considered to be "enriched" or "substantially purified." Such a composition may also include other compounds found in milk or milk isolates, including lactoperoxidase, growth factors, calcium, and other compositions.

In one aspect, a milk-derived lactoferrin product (MDLF) comprises at least about 10% bovine lactoferrin, which may have an iron content of from about 15 mg/100 g to about 40 mg/100 g. In other aspects, the MDLF may comprise at least about 50%, at least about 75%, or at least about 90% lactoferrin. Some forms of MDLF may also comprise the apolactoferrin form of lactoferrin, providing an iron concentration of from about 0 mg/100 g to about 15 mg/100 g. In some embodiments, apolactoferrin may comprise an iron concentration of from about 4 mg/100 g to about 15 mg/100 g.

Bioferrin® 1000 (Glanbia Nutritionals, Inc.) is a natural, biologically-active milk-derived protein product comprising bovine apolactoferrin from fresh sweet whey. It is isolated using fractionation separation techniques known to those of skill in the art and comprises greater than 90 percent protein, with greater than 90% of the total protein (e.g., 95%) comprising lactoferrin, primarily in the apolactoferrin form (<15 mg iron/100 g). Bioferrin® 2000 is a similar product, except that iron is present at a level that is from about 15 to 40 mg/100 grams of product.

A composition comprising bovine lactoferrin in the apolactoferrin form and/or the higher-iron form may be used in the method of the present invention to produce an endotoxin-free product. Generally, for wound care, the apolactoferrin form may provide additional benefits, although both forms have been demonstrated to be effective. Endotoxins are lipopolysaccharide products released when Gram-negative bacteria such as *Escherichia coli* and *Pseudomonas aeruginosa* die. Wounds that are difficult to treat with standard wound-care methods generally contain established biofilm, which is more often than not comprised of a mixed population of microorganisms. Endotoxin production within a biofilm has been reported to be at least approximately 1000 units/cm$^2$ (Rioufol, C. et al. *J. Hosp Infect.* (1999) 43: 203-209). Studies done at the Center for Biofilm Engineering at Montana State University have demonstrated that a log reduction in biofilm associated with hemodialysis tubing is correlated with a linear reduction in endotoxin level. Additional studies done at Montana State's CBE have also demonstrated that a biofilm comprising primarily *Pseudomonas aeruginosa* produces approximately 3,100 to 6,200 (mean 4,300) endotoxin units per square centimeter of biofilm. Chronic wounds are characterized by increased pro-inflammatory cytokines, increased matrix metalloproteases, low levels of tissue inhibitors of matrix metalloproteases, and low levels of growth factor cytokines, as well as degraded receptors on the cells constituting the wound bed (senescent cells). Many of these characteristics have been associated with endotoxin. In the wound environment, endotoxins have been found to stimulate the production of inflammatory mediators such as TNF-α and interleukins, which stimulate production of matrix metalloproteinases (MMPs). Non-healing wounds have been associated with prolonged increased levels of MMPs, which may contribute to the degradation of growth factors, cellular receptors, and other components of healthy tissue. Bacterial endotoxins decrease wound tensile strength, decrease collagen deposition and cross-linking, and have been associated with surgical wound dehiscence (Metzger, Z. et al. (2002) *J. Endod.* 28(1): 30-33.) For an acute wound, especially, an EFL product of the invention may be particularly beneficial, as such a product will limit the potential for cell death and an undesirable immune response in the wound tissue that may slow the wound-healing process.

The invention also provides an endotoxin-free lactoferrin (EFL) made by the aforementioned method. Lactoferrin protein compositions from human or animal origin, made via recombinant DNA technology methods or isolated from milk may be purified by the method of the present invention. EFL may be especially effective for applications where lactoferrin is suggested to provide a benefit, but where the effects of lactoferrin-bound endotoxin are especially undesirable. EFL of the present invention may be incorporated into mouthwash, toothpaste, nutritional drinks, foods, wound care products such as creams, gels, bandages and other wound care products, cosmetic products such as creams, lotions, and gels used for a variety of applications, including anti-aging, acne medication, and other uses. EFL may be used for the treatment of acute and/or chronic wounds. EFL may be provided for all the above-mentioned uses, and for other uses, in combination with other active agents, such as xylitol, antibiotics, antioxidants, and other agents chosen for the particular purpose for which the EFL composition is to be formulated, such as for wound care, oral care, and/or skin care.

A composition comprising bovine milk-derived and/or whey-derived lactoferrin has recently been shown to provide a safe, highly-effective, plentiful and affordable topical wound care agent. Compositions of the present invention have been shown by the inventors to be superior to current commercially-available bovine lactoferrin compositions in terms of promoting cell viability of primary human keratinocytes, a cell type known to be necessary for wound healing. As illustrated by FIGS. 2 through 8, when "low-endotoxin" (i.e., approximately 400 EU/mg) and "medium-endotoxin" (i.e., approximately 0.40 EU/mg) compositions are compared in keratinocyte cell cultures with or without serum added to the media, the addition of the medium-endotoxin product produces significant cell death in both the presence and absence of serum, while cell viability is maintained in the cultures to which the low-endotoxin product is added. For acute wound care, this difference may be especially beneficial. A significant difference between acute and chronic wounds is that chronic wounds are generally associated with the presence of bacterial biofilm. Endotoxins from the bacteria produce a cascade of cellular and immunological effects that is generally considered to delay the wound-healing process. While lactoferrin promotes wound healing, human lactoferrin must generally be derived via recombinant DNA methods which may be expensive and may also yield a protein with associated endotoxin, and bovine lactoferrin, while providing a more readily available source of endotoxin, is also likely to be associated with bound endotoxin. Bovine lactoferrin purified by the method of the invention provides a wound care composition that may be especially effective for application to acute wounds via powders, gels, creams, ointments, bandages, or other compositions/products, as this form of lactoferrin does not introduce endotoxin into the wound environment and, as demonstrated by the experiments described herein, does not contribute to keratinocyte death.

Based on the results of the inventors' comparison between EFL and higher-endotoxin products, they also provide here a method for improving healing in chronic and acute wounds, as well as a method for reducing biofilm formation and reconstitution in conditions that are associated with biofilm formation and reconstitution, which include, but are not limited to, contact-lens-associated keratitis, endophthalmitis, otitis media, chronic tonsillitis, chronic rhinosinusitis, burn wounds, decubitus ulcers, surgical site infections, diabetic foot ulcers, inflammatory bowel disease, peptic ulcers, surface wounds associated with post-operative infection, and vaginosis. A variety of uses for human are described, for example, in U.S. Pat. No. 6,455,687. ELF of the present invention is also suited for use for therapeutic uses which have been identified for human lactoferrin. For these and other conditions associated with biofilm establishment and reconstitution, compositions comprising EFL may be provided and administered as eye drops, ear drops, oral sprays, lozenges, quick-dissolve strips, nasal sprays, sinus irrigation solutions, ointments, creams, gels, components of bandages, tablets, caplets, capsules, liquids, and other use-appropriate compositions that may additionally comprise appropriate excipients, flavorings, colorings, and additional active agents.

Endotoxin-free lactoferrin compositions are especially suited for application to tissues that may be especially endotoxin sensitive, and endotoxin-free lactoferrin compositions of the present invention that are made by the method of the invention may be applied to devices that may be implanted into tissues, such as orthopedic implants, ocular prostheses, contact lenses, and intrauterine contraceptive devices.

Lactoferrin has also been demonstrated to be beneficial as a prophylactic agent against viral infection. For that purpose, it may be provided for oral administration via a variety of vehicles for administration of therapeutic agents, such as, for example, tablets, effervescent tablets, oral strips such as those made of pullulan that may be placed on the tongue, etc., or may be provided, for example, via nasal and/or throat sprays. EFL compositions of the present invention may be especially beneficial for use as nasal sprays. In rats, an animal model for immune response to endotoxin, inhaled endotoxin produces a dose-dependent response in rat nasal and tracheobronchial airways (Gordon, T. and J. R. Harkema, *Am. J. Respir. Cell Mol. Biol.*, Vol. 10, No. 2, p. 177-183 (1994)). EFL compositions of the present invention may therefore provide lactoferrin for use in nasal sprays for prophylactic use against respiratory virus infection, while avoiding the mucous secretions and associated discomfort that may be associated with nasal endotoxin exposure.

In various embodiments, compositions comprising EFL may also comprise at least one additional agent for topical application to a wound, such as, for example, a moisturizing agent, a hydrocolloid gel, a saline composition, a medium-chain dextran (e.g., honey), etc., for application to an acute or chronic wound. Commercially available compositions such as, for example, DuoDerm® Hydroactive Dressings (Bristol-Myers Squibb, Princeton, N.J.), can be used as a base into which a suitable amount of EFL (Bioferrin®, Glanbia Nutritionals, Inc., Monroe, Wis.) is admixed. Moisturizing agents suitable for wound care are known to those of skill in the art, and a number of such agents are commercially available.

A wound healing composition, and a method of healing wounds by administering the composition, may comprise EFL and xylitol. Such a composition may also optionally comprise antimicrobial agents such as antibiotics, moisturizers, or other agents to improve the rate of wound healing, as well as excipients and compositions for facilitating topical application of the EFL/xylitol.

Compositions of the present invention may readily be used in conjunction with compositions and devices containing antimicrobial preparations of silver. Compositions may comprise, for example, EFL or EFL-A, xylitol, and a silver product such as Acticoat® (Smith and Nephew, Memphis, Tenn.). Acticoat®, for example, may provide antimicrobial silver as a rayon/polyester non-woven core laminated between an upper and lower layer of silver-coated high density polyethylene (HDPE) mesh. Acticoat® Moisture Control (Smith and Nephew, Memphis, Tenn.) is a foam dressing comprising silver in nanocrystalline form. Actisorb® Silver products distributed by Johnson and Johnson comprise activated charcoal cloth impregnated with silver (33 µg silver per square cm of cloth). Arglaes® products (Giltech Ltd., UK) also provide polymers for release of silver ions from a powder, film dressing, or other preparation for application to a wound. Compositions of the present invention may be incorporated into such products or used in combination with such products. One advantage of augmenting the use of silver products with the use of compositions described by the invention is the ability to incorporate less silver into the products while achieving an improved effect on wound healing. As used herein in regard to silver-containing wound dressings, both compositions and devices are included, and may include woven or non-woven fabrics or polymers, alginates, foams, powders, gels, creams, liquids, wound fillers and other pharmaceuticals or medical devices deemed by those of skill in the art to be appropriate for effective delivery of silver compositions to a wound.

Activated lactoferrin and methods for producing activated lactoferrin have been described by Naidu in U.S. Pat. No. 6,172,040. Naidu describes the immobilization of lactoferrin on a substrate to which lactoferrin readily binds in order to increase its iron-binding capacity. A composition comprising an activated form of lactoferrin in combination with an EFL may also provide an effective wound care composition.

For acute wound care, EFL compositions of the invention made by the method of the invention may be also applied to a bandage to increase wound healing.

Compositions of the invention may be administered to humans and/or animals and methods for use of such compositions are also suitable for humans and/or animals.

The invention may be further described by means of the following non-limiting examples.

EXAMPLES

Example 1

Preparation of EFL

Ion exchange was performed as described above. Tables 2 and 3 illustrate the results obtained by the method described herein.

TABLE 2

Individual Ion Exchange Lots

| Day/Run | LAL (EU/mg) (Limulus Amibocyte Lysate Plate (Kinetic Technique) Method) |
|---|---|
| 1/1 | 0.701 |
| 1/2 | 0.739 |
| 2/1 | 2.8 |
| 2/2 | 7.356 |
| 2/3 | 6.88 |
| 3/1 | 4 |
| 3/2 | 2.15 |
| 4/2 | 0.07 |
| 5/3 | 1.88 |

TABLE 2-continued

Individual Ion Exchange Lots

| Day/Run | LAL (EU/mg) (Limulus Amibocyte Lysate Plate (Kinetic Technique) Method) |
|---|---|
| 5/4 | 1.95 |
| 5/5 | 1.02 |
| 6/1 | 0.33 |
| 6/2 | 0.39 |
| 6/3 | 0.81 |
| 6/4 | 0.61 |
| 6/5 | 1.54 |
| 7/6 | 2.45 |
| 8/1 | 0.32 |
| 8/2 | 0.958 |
| 8/3 | 1.353 |
| 9/1 | 0.331 |
| 9/2 | 0.199 |
| 9/3 | 0.411 |
| 9/4 | 0.428 |
| 9/5 | 0.255 |
| 9/6 | 0.121 |
| 10/1 | 0.23 |
| 10/2 | 0.12 |
| 10/3 | 0.131 |
| 10/4 | 0.47 |
| 10/5 | 0.258 |
| 11/1 | 1.14 |
| 11/2 | 4.87 |
| 11/3 | 7.413 |
| 11/4 | 2.373 |
| 12/1 | 0.349 |
| 13/1 | 0.327 |
| 13/2 | 0.19 |
| 13/3 | 0.205 |
| 13/4 | 0.125 |
| 13/5 | 0.233 |
| 13/6 | 0.15 |
| 14/1 | 0.299 |
| 14/2 | 0.162 |
| 14/3 | 0.148 |
| 15/1 | 0.2398 |
| 15/2 | 0.137 |
| 15/3 | 0.323 |
| 15/4 | 0.159 |
| 15/5 | 0.0788 |
| 15/6 | 0.091 |
| 15/7 | 0.137 |
| 16/1 | 1.676 |
| 16/2 | 0.731 |
| 16/3 | 0.803 |
| 16/4 | 0.724 |
| 16/5 | 1.015 |
| 17/1 | 0.158 |
| 17/2 | 0.419 |

TABLE 3

Daily Average Results of Limulus Amoebocyte Asssay

| Day | Batches Produced | Average or Comped EU |
|---|---|---|
| 1 | 2 | 0.117 |
| 2 | 6 | 0.275 |
| 3 | 5 | 0.242 |
| 4 | 4 | 1.315 |
| 5 | 1 | 0.349 |
| 6 | 6 | 0.168 |
| 7 | 5 | 0.185 |
| 8 | 7 | 0.179 |
| 9 | 5 | 1.015 |
| 10 | 8 | 0.291 |
| 11 | 9 | 0.465 |

Example 2

Product Comparison in Keratinocyte Scratch Assay, No Serum in Media

Primary human keratinocytes were seeded in 24-well plates and grown to 90-95% confluence. A scratch was made down the center of the well, using a 200 microliter pipet tip. Plates were washed with HEPES-buffered saline and imaged (T=0). Three hundred microliters of product (standard commercially-available bovine lactoferrin product=medium endotoxin, product produced by the method of the invention=low endotoxin) were added to the corresponding wells and cells were incubated at 37° C. at 5% $CO_2$. At 24-hour intervals, media and product were removed by aspiration, cells were washed with buffered saline, and fresh media with product were replaced. Cells were returned to the incubator after washing and media/product change. The assay was terminated after 72 hours. Product tested comprised 1% of the low endotoxin product (EFL) in cell culture medium, 2% of the low endotoxin product (EFL) in cell culture medium, 1% of the high endotoxin product (commercially available product, isolated lactoferrin, no endotoxin removal method used) in cell culture medium, and control (cell culture medium only). Cell culture medium did not contain fetal bovine serum/fetal calf serum.

When the cells were observed for closure of the scratch area, it was noted that although neither of the scratch areas had yet closed, a more notable effect was that the cells treated with high-endotoxin lactoferrin were dead or dying at a rapid rate, although the endotoxin was bound to lactoferrin and presumably neutralized by it.

An XTT assay was performed as follows: after 72 hours, product and media were removed from the plates, cells were washed with HBS, and 300 microliters of each cell culture medium plus 60 microliters XTT were added to each well. As a control, two wells with medium plus XTT, but without cells, were used. The XTT assay measures cleavage of the tetrazolium ring of XTT due to mitochondrial dehydrogenase activity, expected to be higher in viable cells, yielding orange formazan crystals and turning the medium from pink to orange. After 4 hours, medium was sampled and absorbance at 490 nm was measured for each sample. Cell viability was then assayed via Trypan Blue Exclusion.

Example 3

Product Comparison in Cultured Primary Human Keratinocytes, Serum Added

Figure 2:
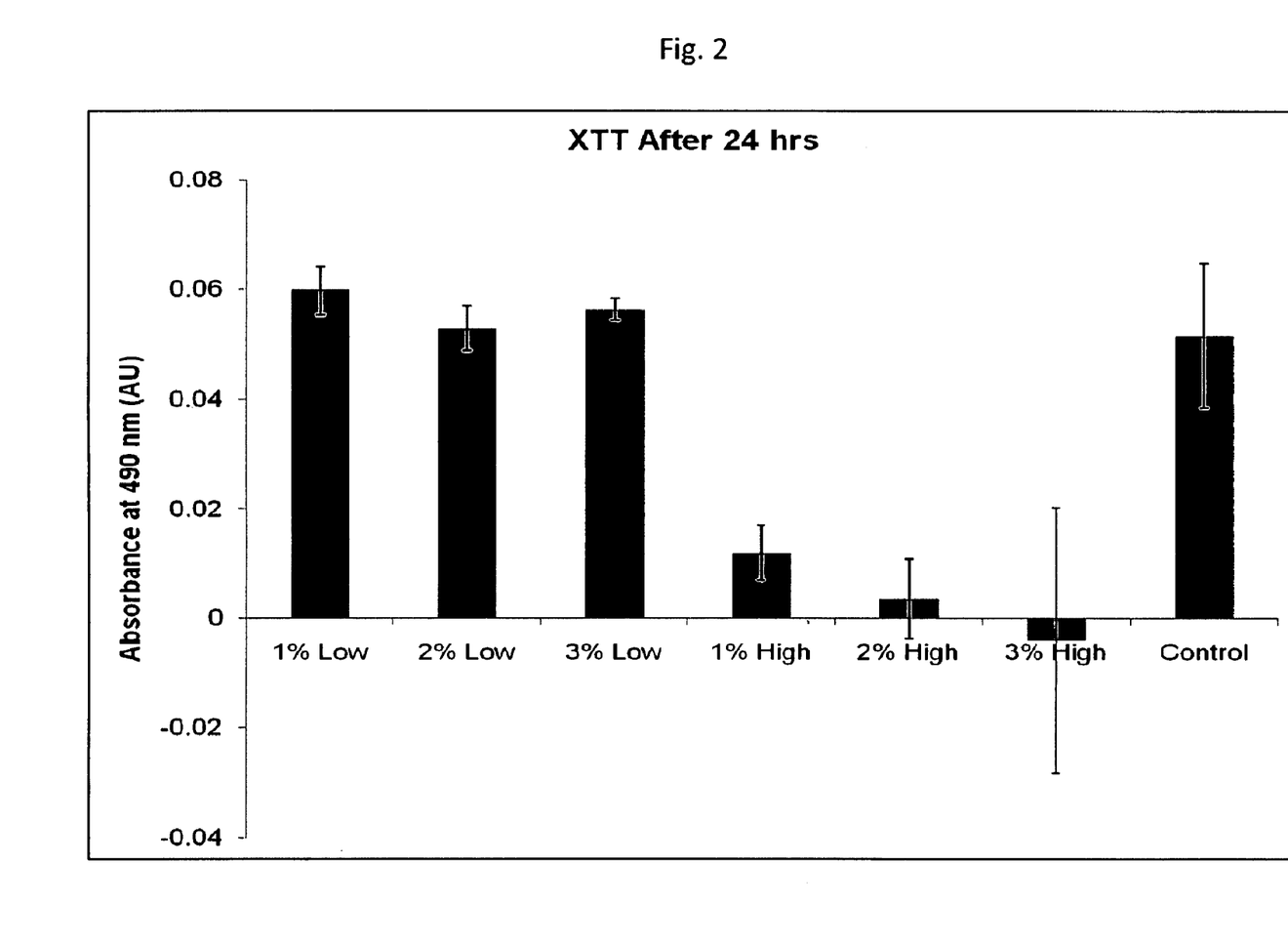
FIG. 2 is a bar graph illustrating the results of an XTT assay performed after 24-hour exposure to the lactoferrin products indicated on the x-axis (media+serum+product).
Figure 3:
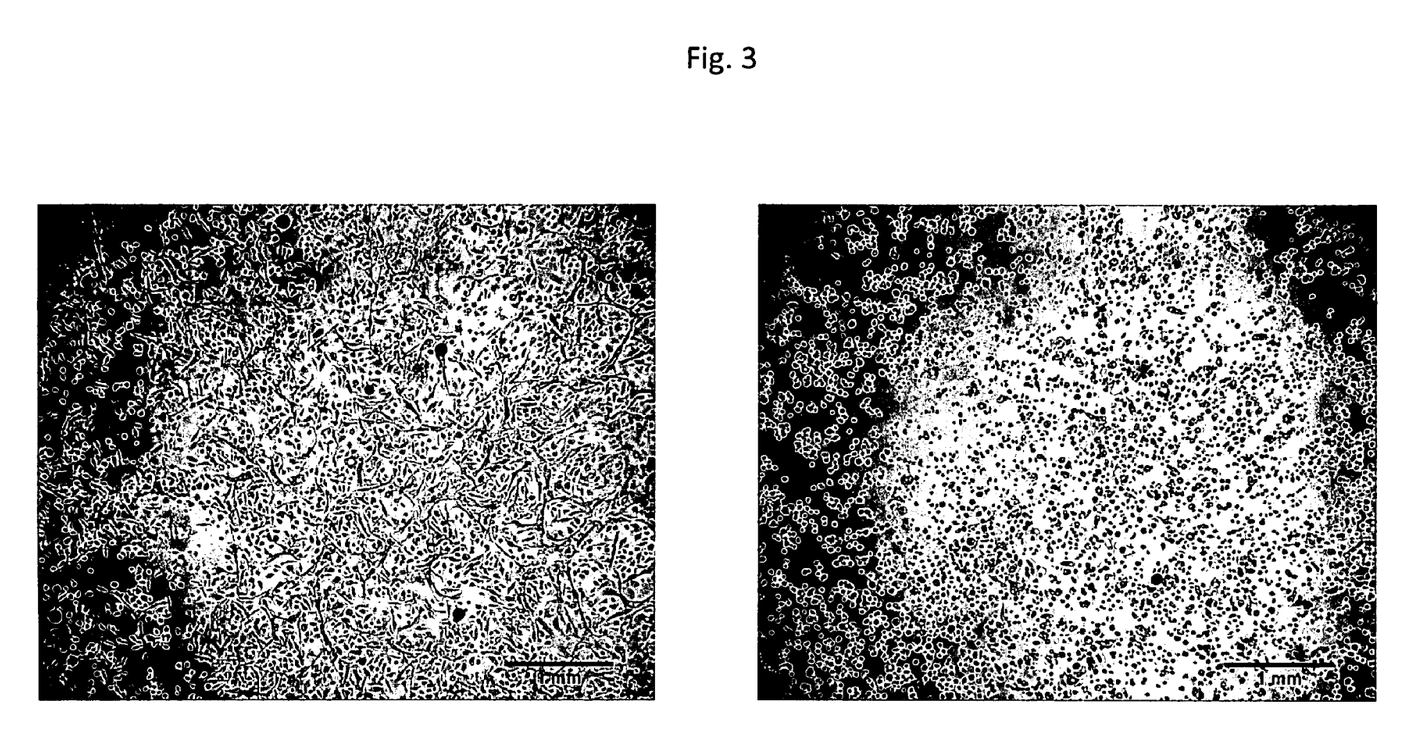
FIG. 3 is a photograph of cells exposed to 1% low-endotoxin lactoferrin (left) and to 1% medium-endotoxin lactoferrin (right). Media contained fetal calf serum.
Figure 4:
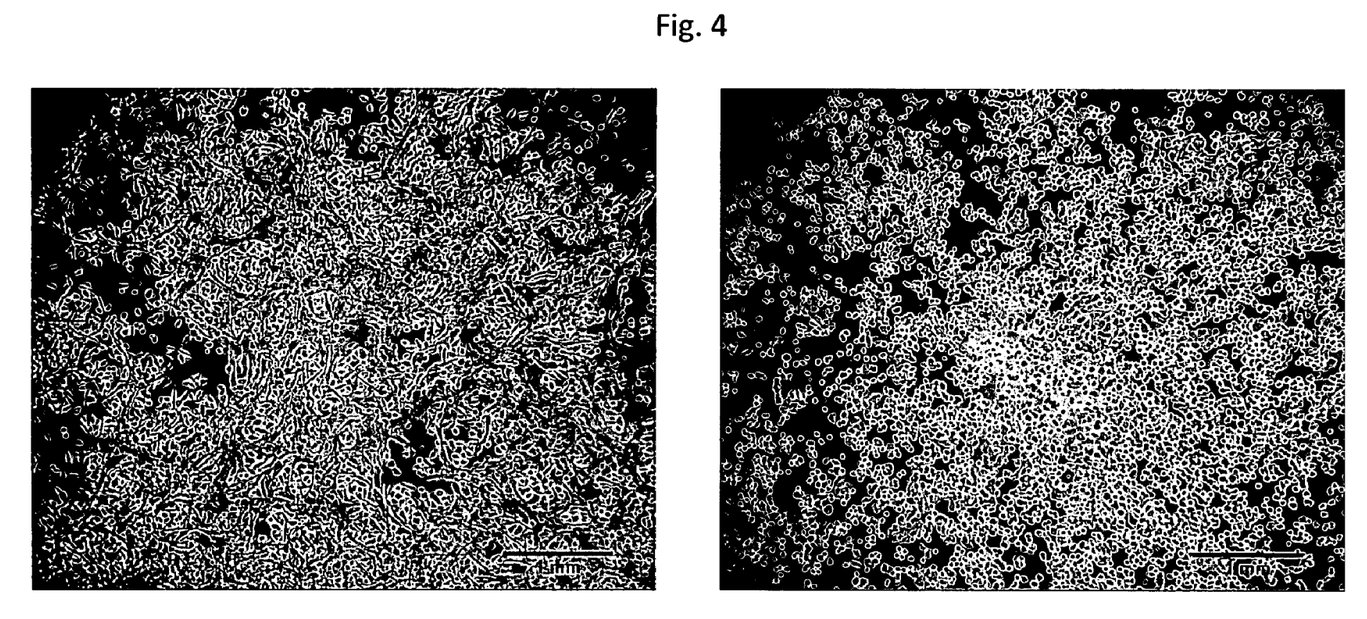
FIG. 4 is a photograph of cells exposed to 2% low-endotoxin lactoferrin (left) and to 2% medium-endotoxin lactoferrin (right). Media contained fetal calf serum.
Figure 5:
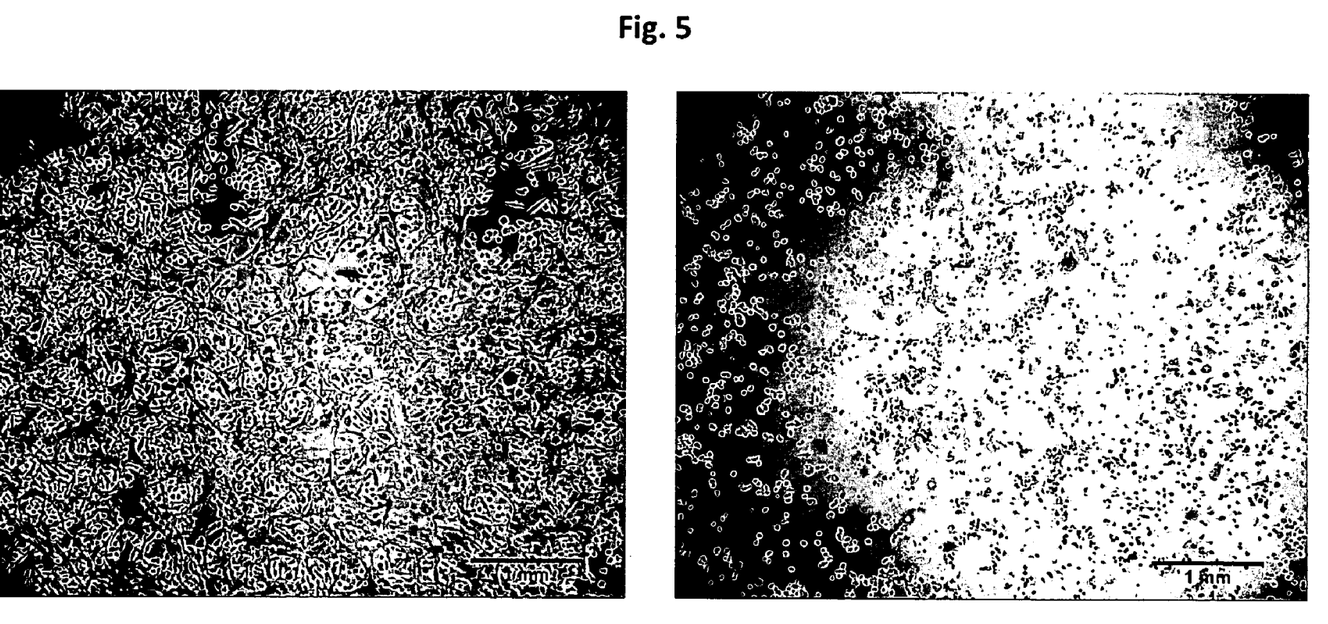
FIG. 5 is a photograph of cells exposed to 3% low-endotoxin lactoferrin (left) and to 3% medium-endotoxin lactoferrin (right). Media contained calf serum.
Figure 6:
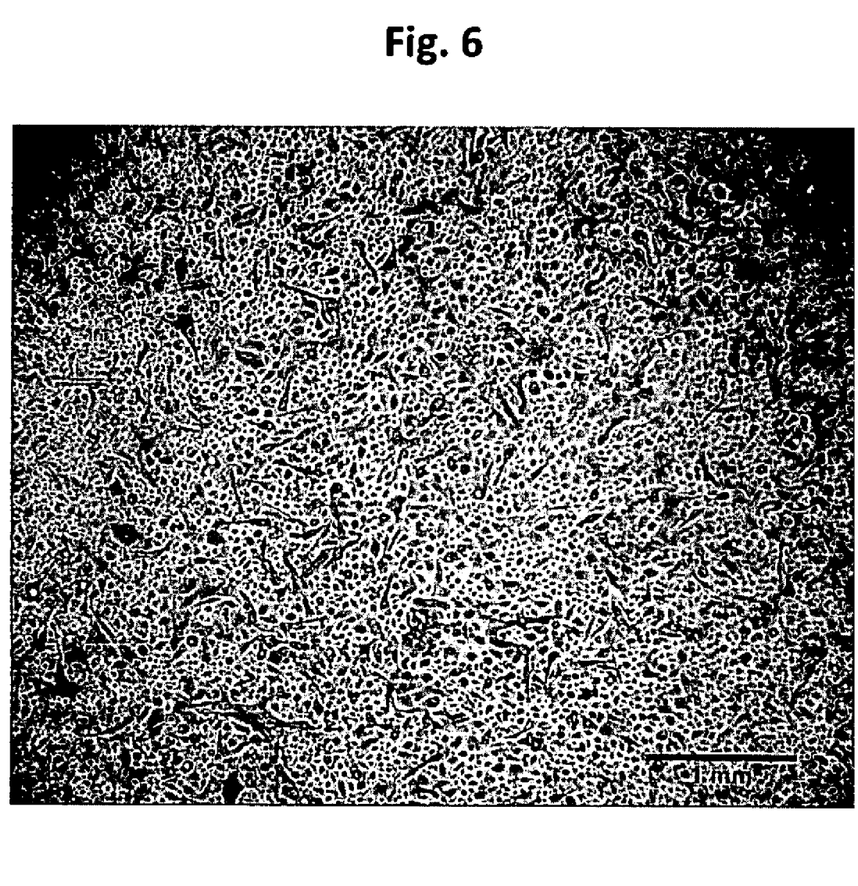
FIG. 6 is a photograph of cells treated as control (EpiLife®+1% fetal calf serum, no lactoferrin added).

Primary human keratinocytes were seeded in 24-well plates and grown to 70% confluence. Plates were washed with HEPES-buffered saline and imaged (T=0). Three hundred microliters of product (standard commercially-available bovine lactoferrin product=medium endotoxin, product produced by the method of the invention=low endotoxin) were added to the corresponding wells and cells were incubated at 37° C. at 5% $CO_2$. Samples tested were 1% low-endotoxin lactoferrin+culture medium, 2% low-endotoxin lactoferrin+culture medium, 3% low-endotoxin lactoferrin+culture medium, 1% medium-endotoxin lactoferrin+culture medium, 2% medium-endotoxin lactoferrin+culture medium, 3% medium-endotoxin lactoferrin+culture medium, and control (cell culture medium only). At 24 hours, media/product was removed, cells were washed, and 300 microliters of fresh medium plus 60 microliters of XTT were added. Cells were incubated for an additional 4 hours, then samples were taken and absorbance was measured at 490 mm. Readings were blanked to controls (cell culture medium+XTT). Results are shown in FIG. 2.

As shown in FIGS. 3-6, application of low-endotoxin product to cells significantly increases cell viability over that seen after application of medium-endotoxin product.

What is claimed is:

1. A product comprising an endotoxin-free protein made by removing bound endotoxin from an endotoxin-binding protein by a method comprising the steps of
    (a) binding the endotoxin-binding protein to a cation exchange resin;
    (b) eluting the bound endotoxin from the endotoxin-binding protein using a low ionic strength solution in the absence of added surfactant; and
    (c) eluting the endotoxin-binding protein from the cation exchange resin with a high ionic strength solution;
    wherein the endotoxin-binding protein is a lactoferrin, lactoferricin, or lactoperoxidase and the endotoxin-free protein comprises less than about 20 endotoxin units per milligram of protein.

2. The product of claim 1 wherein the endotoxin-binding protein is lactoferrin.

3. The product of claim 1 wherein the low ionic strength solution of step (b) is a 0.01 to 0.5 molar salt solution.

4. The product of claim 1 wherein the low ionic strength solution of step (b) is a 0.25 to 0.35 molar salt solution.

5. The product of claim 1 wherein the high ionic strength solution is an 80-100 mS/cm salt solution.

* * * * *